H. EGLI.

ARTIFICIAL LIMB.

APPLICATION FILED OCT. 28, 1918.

Reissued Jan. 25, 1921. 15,034.

WITNESS

Geo. Strong.

INVENTOR

Herman Egli

BY

Redding, Greeley & Goodlett his ATTORNEYS

UNITED STATES PATENT OFFICE.

HERMAN EGLI, OF WEST HOBOKEN, NEW JERSEY, ASSIGNOR TO E-Z FIT ARTIFICIAL LIMB CO. INC., OF NEW YORK, N. Y., A CORPORATION OF NEW YORK.

ARTIFICIAL LIMB.

15,034. Specification of Reissued Letters Patent. Reissued Jan. 25, 1921.

Original No. 1,201,812, dated October 17, 1916, Serial No. 80,113, filed February 24, 1916. Application for reissue filed October 28, 1918. Serial No. 260,036.

*To all whom it may concern:*

Be it known that I, HERMAN EGLI, a citizen of the United States, and resident of West Hoboken, in the county of Hudson and State of New Jersey, have invented an Improved Artificial Limb, of which the following is a specification.

Modern artificial limbs must combine lightness, strength and durability and, for those reasons, were heretofore made of wood, aluminum, rawhide and similar material.

The artificial limb, illustrated in the accompanying drawing, is formed of one continuous strip of sheet material and obtains its final shape, mating a natural limb, by cutting the strip similar in form to the letter S and arranging it into a helix, having suitable means for securing it to the human body and for attaching the necessary joints. While it is preferable to form the helix or winding of a continuous strip having an S shape, it is not always essential that the strip be continuous or of this particular S shape. The material of the strip is a strong, fibrous, sheet material, suitable to the purposes of my invention.

The limb and its details of construction are shown in Figure 1, as a side elevation of the lower leg.

Figure 1:
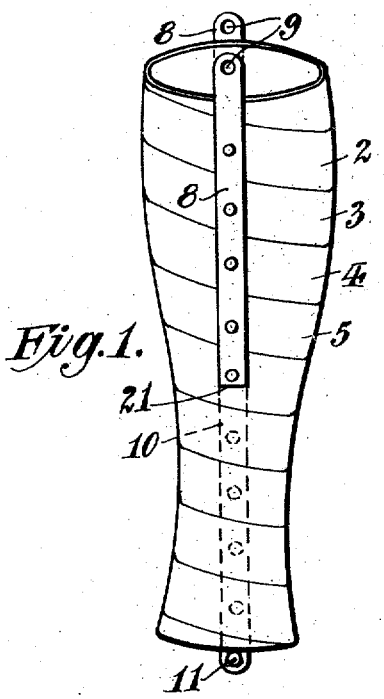
Figure 2:
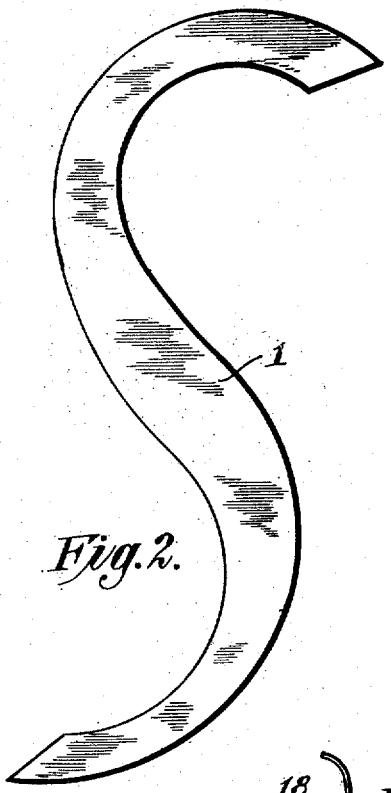
Fig. 2 illustrates one form of the S shaped strip of sheet material.
Figure 3:
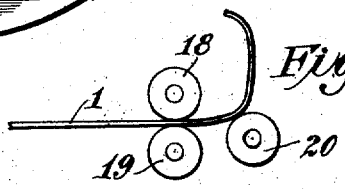
Fig. 3 is a diagrammatic view of a device for shaping the strip into a helix.
Figure 4:
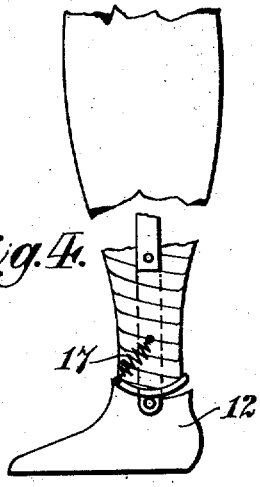
Fig. 4 is a side elevation of the limb with a foot attached.
Figure 5:
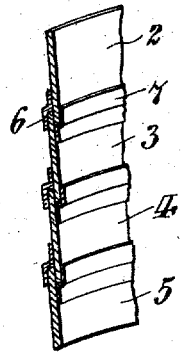
Fig. 5 is a detail of construction of adjoining turns of the helix.
Figure 6:
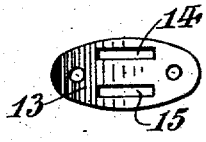
Figs. 6 and 7 are details of construction of the means for securing the foot to the limb.
Figure 7:
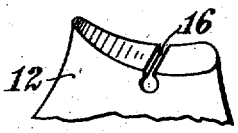

A sheet of fibrous relatively thin material is cut into cyma-form or S shaped elements 1, or other suitable shape, varying in demensions and curvatures according to the size and form of the natural limb to be imitated. This element or templet is first softened and made pliable by, for instance, steaming or heating it and then shaped by rolling it through a device similar to the one shown in Fig. 3, although any other method or apparatus may be employed for this purpose. The rollers 18, 19 and 20, engaging the templet, may be suitably heated, if desired, so that the material first softened is hardened and stiffened again, after having been shaped. The templet, when leaving the rollers, will at once assume the form of a helix, as shown in Fig. 1, formed by abutting turns 2, 3, 4 and 5. The turns of the winding are held in permanent position by suitable means secured to said turns. These means preferably consist of upright metal strips riveted to said turns. In the drawings there are shown two metal strips each consisting of an upper part 8 riveted to the upper turns on the outside and a lower part 10 riveted to the lower turns on the inside. Each strip passes from the outside to the inside through a slit 21. These strips constitute means to hold the turns of the winding in permanent position and may have bearings 9 for the knee joint and bearings 11 for the foot joint. The sides of the abutting turns may be flush, edge to edge, or may overlap, and these abutting edges may be covered by strips of adhesive material 6 and 7, or other convenient means. The helix may be coated with one or more layers of varnish so as to make it moisture proof.

The foot may be carried by having the ends of the lower brace 10, pass a bearing plate 13, provided with slots 14 and 15. A bolt, located in the bearing groove 16, of the foot 12, secures the foot to the bearings 11. A retractile spring 17, or other well known means, is usually provided for giving the foot the necessary resiliency.

What I claim is:

1. The method of producing artificial limbs which consists in, first, providing a continuous cyma-form element of fibrous sheet material, second, shaping the same into helicoidal form, and third, securing together the sides of abutting turns of said helix.

2. An artificial limb comprising a helix formed of a continuous cyma-form element of fibrous sheet material.

3. An artificial limb comprising a helix formed of a continuous element of fibrous sheet material having the sides of abutting turns of said helix overlapping, and means for securing together said abutting turns.

4. An artificial limb comprising a helix formed of strong, fibrous, sheet material, and means secured to and holding the turns of the helix in permanent position.

5. An artificial limb comprising a helix formed of strong, fibrous, sheet material, and means comprising metal strips riveted to and holding the turns of the helix in permanent position.

6. The method of producing an artificial limb which consists in providing a strip of strong, fibrous, sheet material, rendering the same pliable by subjecting it to heat and moisture, shaping the same into the form of a helix, and securing the turns of the helix together in permanent position.

This specification signed this 15th day of October, 1918.

HERMAN EGLI.